United States Patent
Kato et al.

(10) Patent No.: US 10,106,775 B2
(45) Date of Patent: Oct. 23, 2018

(54) METHOD OF PRODUCING MICROGLIAL CELLS

(71) Applicant: KYUSHU UNIVERSITY, NATIONAL UNIVERSITY CORPORATION, Fukuoka-shi, Fukuoka (JP)

(72) Inventors: Takahiro A. Kato, Fukuoka (JP); Masahiro Ohgidani, Fukuoka (JP); Shigenobu Kanba, Fukuoka (JP)

(73) Assignee: KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 0 days.

(21) Appl. No.: 15/110,004

(22) PCT Filed: Jan. 9, 2015

(86) PCT No.: PCT/JP2015/051156
§ 371 (c)(1),
(2) Date: Jul. 6, 2016

(87) PCT Pub. No.: WO2015/105201
PCT Pub. Date: Jul. 16, 2015

(65) Prior Publication Data
US 2016/0333316 A1 Nov. 17, 2016

(30) Foreign Application Priority Data
Jan. 9, 2014 (JP) .................................. 2014-002129

(51) Int. Cl.
*C12N 5/0786* (2010.01)
*G01N 33/50* (2006.01)

(52) U.S. Cl.
CPC ....... *C12N 5/0645* (2013.01); *G01N 33/5055* (2013.01); *C12N 2501/22* (2013.01); *C12N 2501/2334* (2013.01); *C12N 2506/115* (2013.01); *G01N 2800/28* (2013.01); *G01N 2800/30* (2013.01)

(58) Field of Classification Search
CPC ............ C12N 5/0645; C12N 2506/115; C12N 2501/2334; C12N 2501/22; G01N 33/5055
See application file for complete search history.

(56) References Cited

U.S. PATENT DOCUMENTS

2004/0072346 A1 4/2004 Sawada
2009/0304712 A1 12/2009 Takeuchi et al.

FOREIGN PATENT DOCUMENTS

WO WO 2007/088712 A1 8/2007
WO WO 2012/125809 A1 9/2012

OTHER PUBLICATIONS

Etienne D. Foucher et al.: "IL-34 Indices the Differentiation of Human Monocytes into Immunosuppressive Macrophages. Antagonistic Effects of GM-CSF and IFN[gamma]," PLOS ONE, vol. 8, No. 2, Jan. 8, 2013, p. e56045.
Extended European Search Report issued in corresponding European Application No. 15734968.9 dated Jun. 12, 2017.
Kato et al.: "Risperidone significantly inhibits interferon-gamma-induced microglial activation in vitro," Schizophrenia Research, Elsevier, Netherlands, vol. 92, No. 1-3, Apr. 14, 2007, pp. 108-115.
Masahiro Oghidani et al.: "Introducing directly induced microglia-like (iMG) cells from fresh human monocytes: a novel translational research tool for psychiatric disorders," Frontiers in Cellular Neuroscience, vol. 9, May 27, 2015.
Masahiro Ohgidani et al: "Modeling brain diseases with direct induction technology of ramified microglia-like (iMG) cells from human monocytes," Journal of Neuroimmunology, vol. 275, No. 1, Oct. 15, 2014, p. 120.
Salida Mirzoeva et al: "Screening in a cell-based assay for inhibitors of microglial nitric oxide production reveals calmodulin-regulated protein kinases as potential drug discovery targets," Brain Research, vol. 844, No. 1-2, Oct. 1, 1999, pp. 126-134.
Aloisi et al., "Functional Maturation of Adult Mouse Resting Microglia into an APC is Promoted by Granulocyte-Macrophage Colony-Stimulating Factor and Interaction with Th1 Cells," The Journal of Immunology, vol. 164, 2000, pp. 1705-1712.
Block et al., "Microglia-mediated neurotoxicity: uncovering the molecular mechanisms," Nature Reviews Neuroscience, vol. 8, Jan. 2007, pp. 57-69.
Dimos et al., "Induced Pluripotent Stem Cells Generated from Patients with ALS Can Be Differentiated into Motor Neurons," Science, vol. 321, Aug. 29, 2008 (published online Jul. 31, 2008), pp. 1218-1221 (5 pages total).
Erblich et al., "Absence of Colony Stimulation Factor-1 Receptor Results in Loss of Microglia, Disrupted Brain Development and Olfactory Deficits," PLOS One, vol. 6, Iss. 10, Oct. 27, 2011, pp. 1-13.
Ginhoux et al., "Fate Mapping Analysis Reveals That Adult Microglia Derive from Primitive Macrophages," Science, vol. 330, Nov. 5, 2010 (published online Oct. 21, 2010), pp. 841-845 (6 pages total).
Graeber, "Changing Face of Microglia," Science, vol. 330, Nov. 5, 2010, pp. 783-788 (7 pages total).
Hakola, "Neuropsychiatric and Genetic Aspects of a New Hereditary Disease Characterized by Progressive Dementia and Lipomembranous Polycystic Osteodysplasia," Acta Psychiatrica Scandinavica Supplementum, vol. 232, 1972, pp. 10-173 (89 pages total).
Hamerman et al., "Enhanced Toll-like receptor responses in the absence of signaling adaptor DAP12," Nature Immunology, vol. 6, No. 6, Jun. 2005 (published online May 15, 2005), pp. 579-586 (9 pages total).
Hanisch et al., "Microglia: active sensor and versatile effector cells in the normal and pathologic brain," Nature Neuroscience, vol. 10, No. 11, Nov. 2007 (published online Oct. 26, 2007), pp. 1387-1394.

(Continued)

*Primary Examiner* — Daniel C Gamett
(74) *Attorney, Agent, or Firm* — Birch, Stewart, Kolasch & Birch, LLP

(57) ABSTRACT

The present invention provides a method of inducing microglia cells from blood cells, comprising culturing the blood cells in the presence of interleukin-34 (IL-34) and granulocyte-macrophage colony stimulating factor (GM-CSF).

7 Claims, 5 Drawing Sheets
(3 of 5 Drawing Sheet(s) Filed in Color)
Specification includes a Sequence Listing.

(56) References Cited

OTHER PUBLICATIONS

Hinze et al., "Microglia differentiation using a culture system for the expansion of mice non-adherent bone marrow stem cells," Journal of Inflammation, vol. 9, No. 12, 2012, pp. 1-9.
International Search Report (Form PCT/ISA/210), dated Apr. 21, 2015, for International Application No. PCT/JP2015/051156.
Kaneko et al., "Nasu-Hakola disease: The first case reported by Nasu and review," Japanese Society of Neuropathology, vol. 30, 2010 (published online May 24, 2010), pp. 463-470.
Kato et al., "Neurotransmitters, Psychotropic Drugs and Microglia: Clinical Implications for Psychiatry," Current Medicinal Chemistry, vol. 20, No. 3, 2013, pp. 331-344.
Kettenmann et al., "Physiology of Microglia," Physiological Reviews, vol. 91, Apr. 2011, pp. 461-553.
Mattis et al., "Induced pluripotent stem cells: a new revolution for clinical neurology?," Lancet Neurology, vol. 10, Apr. 2011, pp. 383-394.
Melief et al., "Phenotyping Primary Human Microglia: Tight Regulation of LPS Responsiveness," GLIA, vol. 60, 2012 (Published online Jun. 27, 2012), pp. 1506-1517.
Mizutani et al., "The Fractalkine Receptor but Not CCR2 is Present on Microglia from Embryonic Development throughout Adulthood," The Journal of Immunology, vol. 188, 2012 (published online Nov. 11, 2011), pp. 29-36 (9 pages total).
Nandi et al., "The CSF-1 receptor ligands IL-34 and CSF-1 exhibit distinct developmental brain expression patterns and regulate neural progenitor cell maintenance and maturation," Developmental Biology, vol. 367, 2012 (available online Apr. 19, 2012), pp. 100-113.
Nasu et al., "A Lipid Metabolic Disease—'Membranous Lipodystrophy'—An Autopsy Case Demonstrating Numerous Peculiar Membrane-Structures . . . And Bone Marrow and Various Adipose Tissues," Acta Pathology Japan, vol. 23, No. 3, 1973, pp. 539-558.
Nimmerjahn et al., "Resting Microglial Cells Are Highly Dynamic Surveillants of Brain Parenchyma in Vivo," Science, vol. 308, May 27, 2005, pp. 1314-1318 (6 pages total).
Noto et al., "In vitro differentiation of lineage-negative bone marrow cells into microglia-like cells," European Journal of Neuroscience, vol. 31, 2010, pp. 1155-1163.
Noto et al., "P-22 Induction of differentiation from peripheral blood monocytes into microglia in mice and humans," The 23th Annual Meeting of the Japanese Society for Neuroimmunology Neuroimmunology Abstracts, Sep. 15-17, 2011, p. 105 (4 pages total), with an English translation thereof.
Ohgidani et al., "Direct induction of ramified microglia-like cells from human monocytes: Dynamic microglial dysfunction in Nasu-Hakola disease," Scientific Reports, vol. 4, May 14, 2014, pp. 1-7.
Paloneva et al., "CNS manifestations of Nasu-Hakola disease: A frontal dementia with bone cysts," Neurology, vol. 56, Jun. 2001, pp. 1552-1558.
Paloneva et al., "Loss-of-function mutations in TYROBP (DAP12) result in a presenile dementia with bone cysts," Nature Genetics, vol. 25, Jul. 2000, pp. 357-361.
Paloneva et al., "Mutations in Two Genes Encoding Different Subunits of a Receptor Signaling Complex Result in an Identical Disease Phenotype," American Journal of Human Genetics, vol. 71, 2002 (electronically published Jun. 21, 2002), pp. 656-662.
Pang et al., "Induction of human neuronal cells by defined transcription factors," Nature, vol. 476, Aug. 11, 2011 (published online May 26, 2011), pp. 220-224.
Paradowska-Gorycka et al., "Structure, expression pattern and biological activity of molecular complex TREM-2/DAP12," Human Immunology, vol. 74, 2013 (available online Feb. 28, 2013), pp. 730-737.
Pfisterer et al., "Direct conversion of human fibroblasts to dopaminergic neurons," PNAS, vol. 108, No. 25, Jun. 21, 2011, pp. 10343-10348.
Qiang et al., "Directed Conversion of Alzheimer's Disease Patient Skin Fibroblasts into Functional Neurons," Cell, vol. 146, Aug. 5, 2011, pp. 359-371.
Ransohoff et al., "Microglial Physiology: Unique Stimuli, Specialized Responses," Annual Review of Immunology, vol. 27, 2009 (published online Dec. 3, 2008), pp. 119-145.
Roumier et al., "Impaired Synaptic Function in the Microglial KARAP/DAP12-Deficient Mouse," The Journal of Neuroscience, vol. 24, No. 50, Dec. 15, 2004, pp. 11421-11428.
Satoh et al., "Immunohistochemical characterization of microglia in Nasu-Hakola disease brains," Neuropathology, vol. 31, 2011 (published online Dec. 1, 2010), pp. 363-375.
Sedgwick et al., "Isolation and direct characterization of resident microglial cells from the normal and inflamed central nervous system," Proceedings of the National Academy of Sciences, vol. 88, Aug. 1991, pp. 7438-7442.
Wang et al., "IL-34 is a tissue-restricted ligand of CSF1R required for the development of Langerhans cells and microglia," Nature Immunology, vol. 13, No. 8, Aug. 2012 (published online Jun. 24, 2012), pp. 753-762.
Wootla et al., "Is Multiple Sclerosis an Autoimmune Disease?", Autoimmune Diseases, vol. 2012, Article ID 969657, 12 pages, doi:10.1155/2012/969657.

SEQUENCE LISTING

<160> NUMBER OF SEQ ID NOS: 16

<210> SEQ ID NO 1
<211> LENGTH: 23
<212> TYPE: DNA
<213> ORGANISM: Artificial

<220> FEATURE:
<223> OTHER INFORMATION: synthetic DNA

<400> SEQUENCE: 1
ttcaggaatc agaaaggaca ctc                                              23

<210> SEQ ID NO 2
<211> LENGTH: 20
<212> TYPE: DNA
<213> ORGANISM: Artificial
<220> FEATURE:
<223> OTHER INFORMATION: synthetic DNA

<400> SEQUENCE: 2
tctgcatttc agctcaggaa                                                  20

<210> SEQ ID NO 3
<211> LENGTH: 27
<212> TYPE: DNA
<213> ORGANISM: Artificial
<220> FEATURE:
<223> OTHER INFORMATION: synthetic DNA

<400> SEQUENCE: 3
agtcaaagtt attgttatgc tgacaga                                          27

<210> SEQ ID NO 4
<211> LENGTH: 20
<212> TYPE: DNA
<213> ORGANISM: Artificial
<220> FEATURE:
<223> OTHER INFORMATION: synthetic DNA

<400> SEQUENCE: 4
tgctttcctt ctccccagta                                                  20

<210> SEQ ID NO 5
<211> LENGTH: 21
<212> TYPE: DNA
<213> ORGANISM: Artificial
<220> FEATURE:
<223> OTHER INFORMATION: synthetic DNA

<400> SEQUENCE: 5
cagcctcttc tccttcctga t                                                21

<210> SEQ ID NO 6
<211> LENGTH: 20
<212> TYPE: DNA
<213> ORGANISM: Artificial
<220> FEATURE:
<223> OTHER INFORMATION: synthetic DNA

<400> SEQUENCE: 6
gccagagggc tgattagaga                                                  20

<210> SEQ ID NO 7
<211> LENGTH: 19
<212> TYPE: DNA
<213> ORGANISM: Artificial
<220> FEATURE:
<223> OTHER INFORMATION: synthetic DNA

<400> SEQUENCE: 7
ggggaaacca atgaaaagc                                                   19

```
<210> SEQ ID NO 8
<211> LENGTH: 22
<212> TYPE: DNA
<213> ORGANISM: Artificial
<220> FEATURE:
<223> OTHER INFORMATION: synthetic DNA

<400> SEQUENCE: 8
acctcatctt gacacaggca ta                                              22

<210> SEQ ID NO 9
<211> LENGTH: 18
<212> TYPE: DNA
<213> ORGANISM: Artificial
<220> FEATURE:
<223> OTHER INFORMATION: synthetic DNA

<400> SEQUENCE: 9
atggccctct gctcctgt                                                   18

<210> SEQ ID NO 10
<211> LENGTH: 22
<212> TYPE: DNA
<213> ORGANISM: Artificial
<220> FEATURE:
<223> OTHER INFORMATION: synthetic DNA

<400> SEQUENCE: 10
aatctgccag gaggtataga cg                                              22

<210> SEQ ID NO 11
<211> LENGTH: 20
<212> TYPE: DNA
<213> ORGANISM: Artificial
<220> FEATURE:
<223> OTHER INFORMATION: synthetic DNA

<400> SEQUENCE: 11
tgggattcat ttggttgttg                                                 20

<210> SEQ ID NO 12
<211> LENGTH: 27
<212> TYPE: DNA
<213> ORGANISM: Artificial
<220> FEATURE:
<223> OTHER INFORMATION: synthetic DNA

<400> SEQUENCE: 12
caactggagt agattctgtt ttattca                                         27

<210> SEQ ID NO 13
<211> LENGTH: 20
<212> TYPE: DNA
<213> ORGANISM: Artificial
<220> FEATURE:
<223> OTHER INFORMATION: synthetic DNA

<400> SEQUENCE: 13
gagaccgagt cgccttatca                                                 20

<210> SEQ ID NO 14
<211> LENGTH: 20
<212> TYPE: DNA
<213> ORGANISM: Artificial
<220> FEATURE:
<223> OTHER INFORMATION: synthetic DNA
```

```
<400> SEQUENCE: 14
ctgtgtgttg aggtcgctgt                                              20

<210> SEQ ID NO 15
<211> LENGTH: 20
<212> TYPE: DNA
<213> ORGANISM: Artificial
<220> FEATURE:
<223> OTHER INFORMATION: synthetic DNA

<400> SEQUENCE: 15
tctgagagct tcgaggatgc                                              20

<210> SEQ ID NO 16
<211> LENGTH: 20
<212> TYPE: DNA
<213> ORGANISM: Artificial
<220> FEATURE:
<223> OTHER INFORMATION: synthetic DNA

<400> SEQUENCE: 16
ggggatttct ccttccaaga                                              20
```

METHOD OF PRODUCING MICROGLIAL CELLS

FIELD OF THE INVENTION

The present invention relates to a method of producing microglial cells from blood cells. More specifically, the present invention relates to a novel technique of developing directly induced microglial (iMG) cells from human peripheral blood cells by using a combination of GM-CSF and interleukin-34.

BACKGROUND OF THE INVENTION

Microglia, immune cells in the brain, play major immunological/inflammatory roles as brain macrophage in the central nerve system (CNS). The origin of resident microglia proved to be from primitive myeloid progenitors (primitive macrophage) that arise in the yolk sac before embryonic day 8 (1). Resident microglia form as a ramified type (called ramified microglia), whose branches constantly move and survey the microenvironment under physiological conditions in the CNS (2), and once activated, shift the form of an ameboid type, phagocytose, and release various mediators such as inflammatory cytokines (3-5). Microglia are suggested to contribute to the pathophysiology of various neurological and psychiatric disorders (6-8). NasuHakola disease (NHD) is a very rare autosomal recessive disorder, initially reported in Finland and Japan (9, 10), which is believed to be caused by microglial dysfunction. Until now, only about 200 cases have been reported worldwide and the majority of cases are in the Finnish and Japanese populations (11). NHD is characterized by formation of multifocal bone cysts and progressive early-onset dementia with various psychiatric symptoms including personality changes (11, 12), caused by mutations of DNAX-activation protein 12 (DAP12) (13) or triggering receptor expressed on myeloid cells 2 (TREM2) (14), both of which are expressed in human microglia. A rodent brain study showed that DAP12 is expressed only in microglia and deletion of DAP12 induces synaptic impairments possibly due to microglial dysfunction (15). A human postmortem study has revealed the absence of DAP12 expression on ramified microglia in brains of NHD (16).

Above-mentioned reports have strongly supported that human microglial cells maladaptively contribute to a variety of neurological and psychiatric disorders including NHD, while the dynamic microglial dysfunction in human brain have not been clarified. The most significant limitation in human brain research is the difficulty in obtaining living brain cells including microglial cells from living human brains based on ethical and technical perspectives. To solve this limitation, alternative methods have long been warranted. Presently, human neuronal cells can be established from somatic cells (not from the brain) such as skin fibroblasts by utilizing the gene-modification technique of induced pluripotent stem (iPS) cells (17, 18). In addition, recently, neuronal cells are more easily established from direct conversion of human skin fibroblasts, called induced neuronal (iN) cells (19-21). Novel methods of establishing ramified microglia from human somatic cells are strongly warranted, based on iPS or direct conversion techniques, while none have yet been reported.

SUMMARY OF THE INVENTION

An object of the present invention relates to a method for inducing or producing microglial cells from blood cells. In the present invention, we tried to develop an induced microglial cells from human monocytes. The present invention provides as follows.

(1) A method of inducing microglial cells from blood cells, comprising culturing the blood cells in the presence of interleukin-34 (IL-34) and granulocyte-macrophage colony stimulating factor (GM-CSF).

(2) A method of producing microglial cells, comprising culturing blood cells in the presence of interleukin-34 (IL-34) and granulocyte-macrophage colony stimulating factor (GM-CSF), and collecting microglial cells from the culture.

(3) The method of (1) or (2), wherein the blood cells are human peripheral monocytes.

(4) The method of (1) or (2), wherein a concentration of IL-34 is 1-200 ng/ml.

(5) The method of (1) or (2), wherein a concentration of GM-CSF is 1-200 ng/ml.

(6) A microglial cell obtained by the method of any one of (1) to (5).

(7) A kit for inducing microglial cells from blood cells, comprising interleukin-34 (IL-34) and granulocyte-macrophage colony stimulating factor (GM-CSF).

(8) A method of screening a therapeutic drug for a psychiatric disease or a neurodegenerative disease, comprising the steps of: causing the microglial cell according to (6) to make contact with a candidate substance to measure a cellular activity of the cell; and using the obtained measurement result as an indicator.

(9) The method according to (8), wherein the cellular activity is at least one selected from the group consisting of phagocytosis, proliferation capacity, viability, neurite elongation capability, cytokine production, morphological changes and differentiation capacity.

(10) The method according to (8) or (9), wherein the psychiatric disease or neurodegenerative disease is at least one selected from the group consisting of schizophrenia, mood disorder, dementia, autism, amyotrophic lateral sclerosis (ALS), Parkinson's disease, Huntington's chorea, prion disease, multiple sclerosis, and physical diseases.

(11) The method according to (10), wherein the physical diseases are autoimmune disorders, atopic disorders or diabetes.

(12) A method of evaluating a responsiveness of a therapeutic drug for a psychiatric disease or a neurodegenerative disease, comprising the steps of: causing the microglial cell according to (6) to make contact with a candidate substance to measure a cellular activity of the cell; and using the obtained measurement result as an indicator.

(13) The method according to (11), wherein the cellular activity is at least one selected from the group consisting of phagocytosis, proliferation capacity, viability, neurite elongation capability, cytokine production, morphological changes and differentiation capacity.

(14) The method according to (12) or (13), wherein the psychiatric disease or neurodegenerative disease is at least one selected from the group consisting of schizophrenia, mood disorder, dementia, autism, amyotrophic lateral sclerosis (ALS), Parkinson's disease, Huntington's chorea, prion disease, multiple sclerosis, and physical diseases.

(15) A kit for screening or evaluating a therapeutic drug for a psychiatric disease or a neurodegenerative disease, comprising a microglial cell according to (6).

(16) A pharmaceutical composition for treating a psychiatric disease or a neurodegenerative disease, comprising a microglial cell according to (6).

BRIEF DESCRIPTION OF THE DRAWINGS

The patent or application file contains at least one color drawing. Copies of this patent or patent application publication with color drawing will be provided by the USPTO upon request and payment of the necessary fee.

The monocytes (A) were incubated with the following candidate cytokines; GM-CSF (10 ng/ml; B), M-CSF (10 ng/ml; C), IL-34 (100 ng/ml; D), M-CSF+IL-34 (E) and GM-CSF+IL-34 (F) for 14 days. The optimal cytokine conditions were tested by morphological changes using phase-contrast microscopy. The cocktail of both GM-CSF and IL-34 induced small soma body bearing numerous branched collaterals, which expressed the specific morphology of ramified microglia (F). Scale bar, 50 μm.

Figure 2:
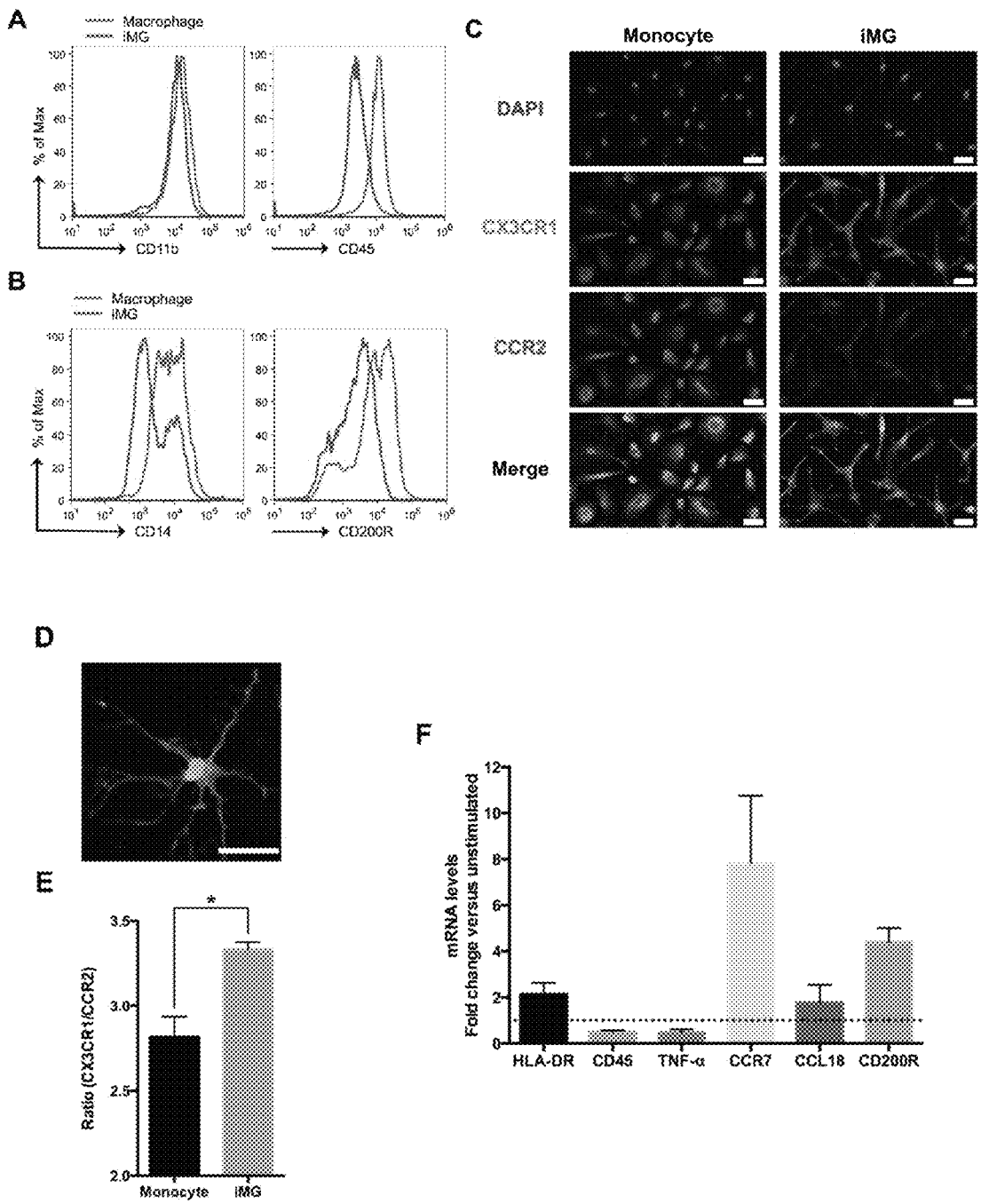

FIG. 2. The iMG cells show the character of human resident microglia.

(A and B) The surface phenotyping of the iMG cells and induced macrophage were performed by flow cytometer. Peripheral monocytes were incubated with GM-CSF (macrophage) or cocktail of GM-CSF and IL-34 (iMG cells) for 14 days. The expression levels of surface marker were measured using flow cytometer. The iMG cells showed the specific phenotypes of microglia compared to macrophage. (C to E) The expression pattern of CCR2 and CX3CR1 between monocytes and iMG cells were observed by immunocytochemistry. The monocytes and iMG cells were cultured for 14 days, and stained with specific antibodies. (C and D) The iMG cells were stained with bright green fluorescence (CX3CR1) bearing highly branched form. Scale bar, 50 μm. (E) The expression ratio (CX3CR1/CCR2) of iMG cells was significantly higher than that of monocytes by immunocytochemistry (n=9). (F) The iMG cells were incubated with IL-4 (40 ng/ml) for 72 hours, and extracted RNA was analyzed by qRT-PCR (n=6). Fold changes are depicted in mRNA levels after stimulation compared with non-treated control. ***P<0.001. Error bars, standard error of the mean (SEM).

Figure 3:
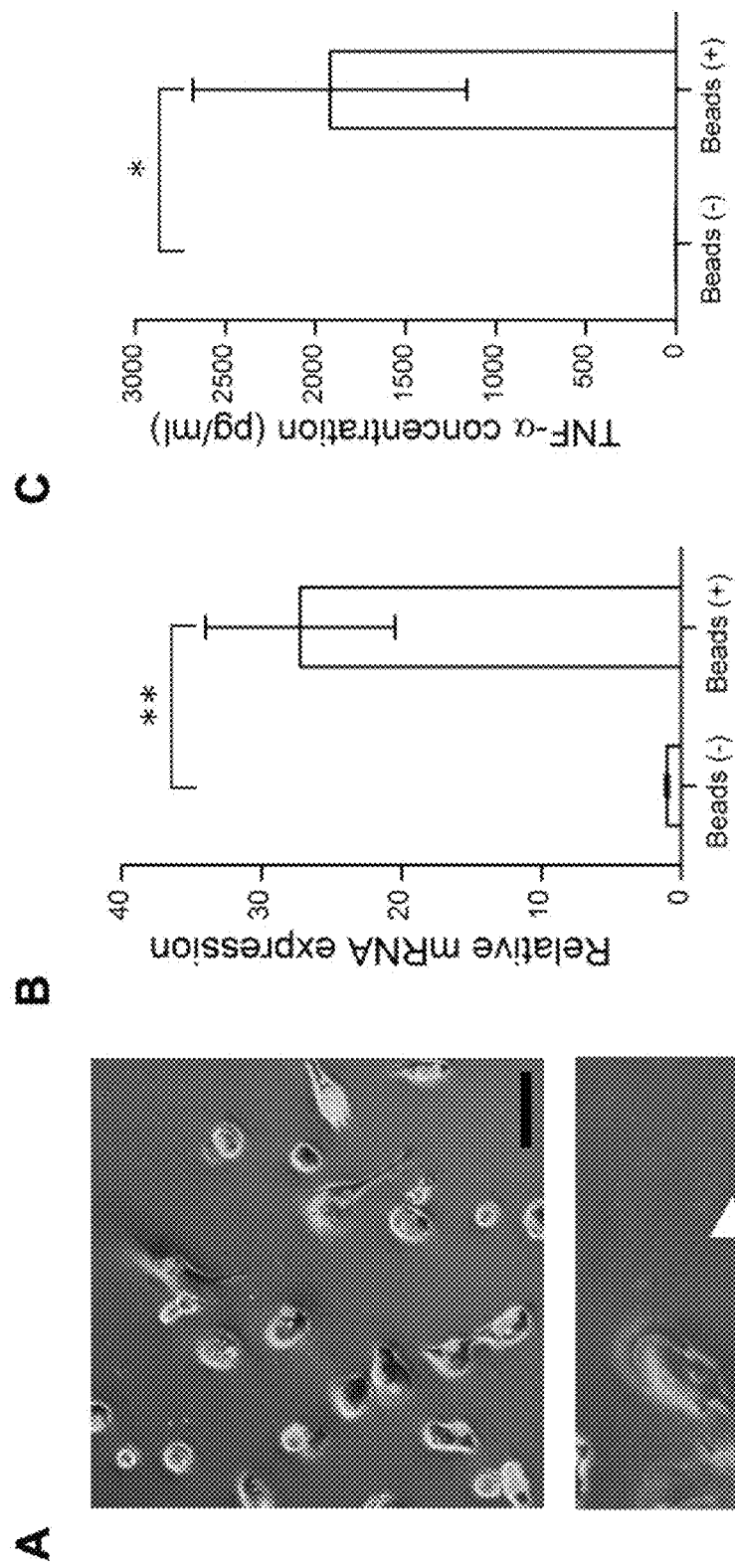

FIG. 3. Dynamic functional analysis of the iMG cells.

(A) The iMG cells were incubated with FITC-conjugated latex beads for 24 hours, and phagocytic activity was observed by fluorescent microscopy. The iMG cells showed the ability of phagocytosis with morphological changes into an ameboid form (arrow head). Scale bar, 50 μm. (B and C) The ability of TNF-α production during phagocytosis was measured on iMG cells. The iMG cells were incubated with latex beads for 72 hours. The extracted RNA and culture supernatant were analyzed by qRT-PCR and Cytometric Beads Array System (CBA), respectively. The mRNA expression (B) and protein level of TNF-α (C) on the iMG cells were significantly higher compared to controls (B, n=4; C, n=6). *P<0.05, **P<0.01. Error bars, SEM.

Figure 4:
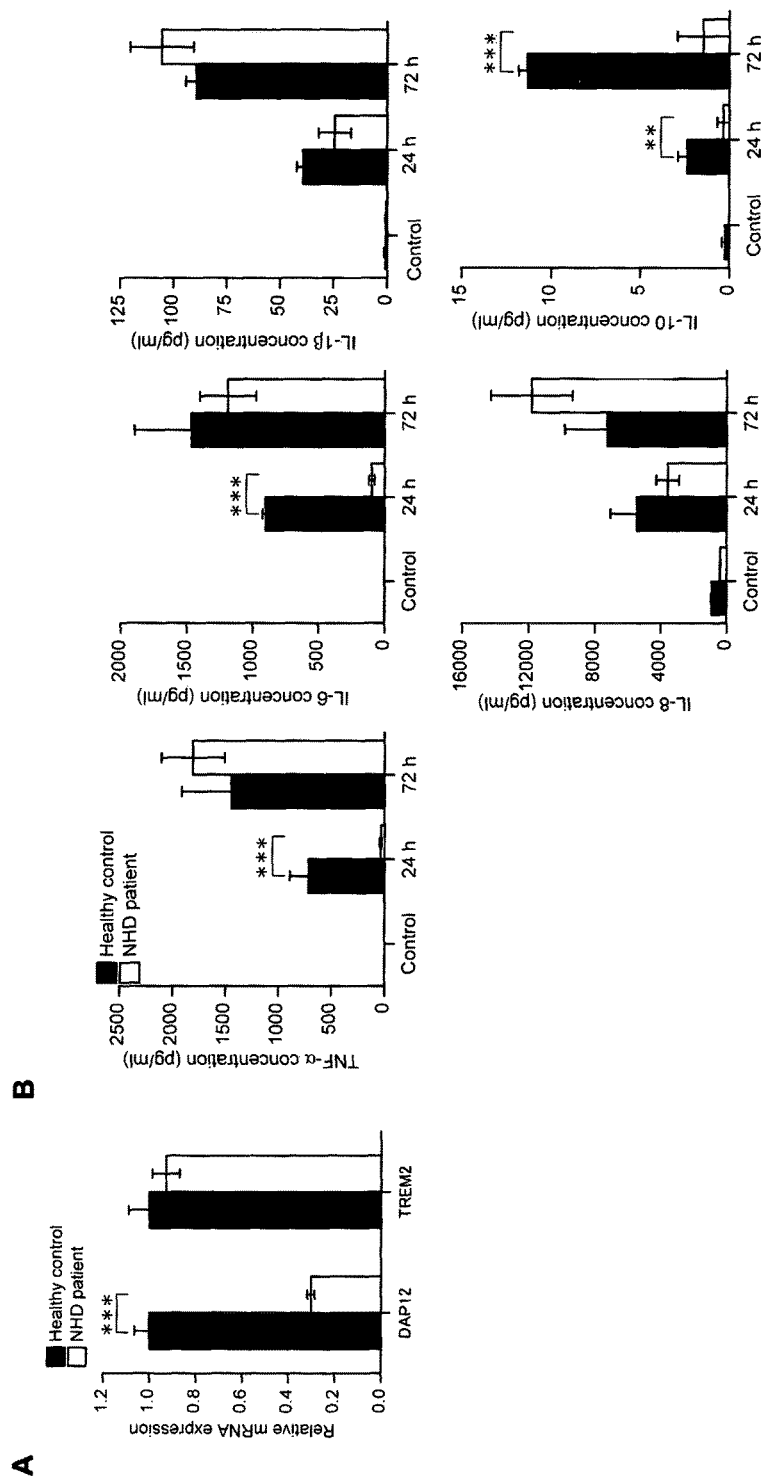

FIG. 4. Dynamic functional analysis of the iMG cells from a patient of NHD.

(A) The iMG cells from NHD showed significantly lower gene expression of DAP12 compared to those from healthy control (n=6). (B) Cytokine productions from the iMG cells were compared between NHD and healthy control. The iMG cells from NHD and healthy control were incubated with latex beads for 24 or 72 hours, and culture supernatants were analyzed by CBA. In the iMG cells from NHD, the production of pro-inflammatory cytokines (TNF-α and IL-6) was delayed, and that of anti-inflammatory cytokine (IL-10) was decreased (n=4). P<0.01, *P<0.001. Error bars, SEM.

Figure 5:
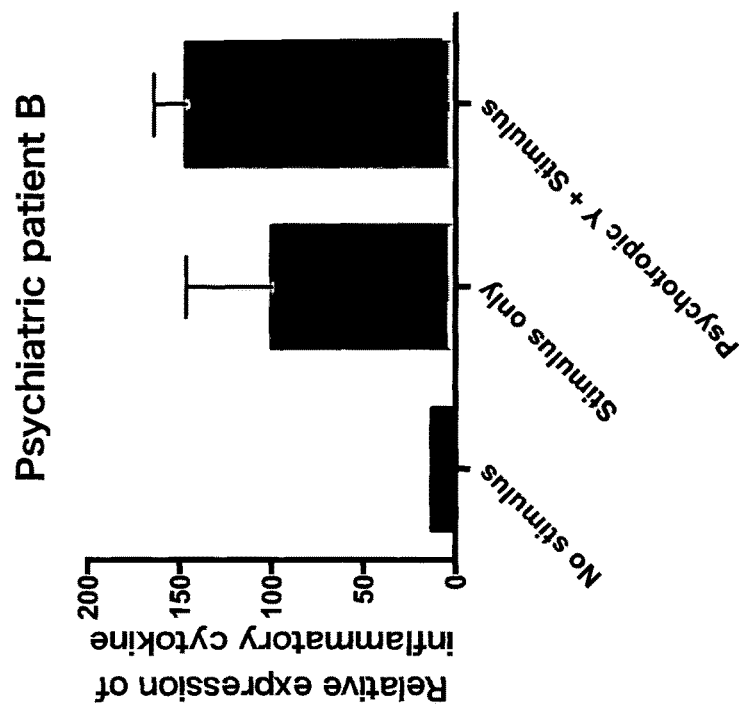
Figure 5:
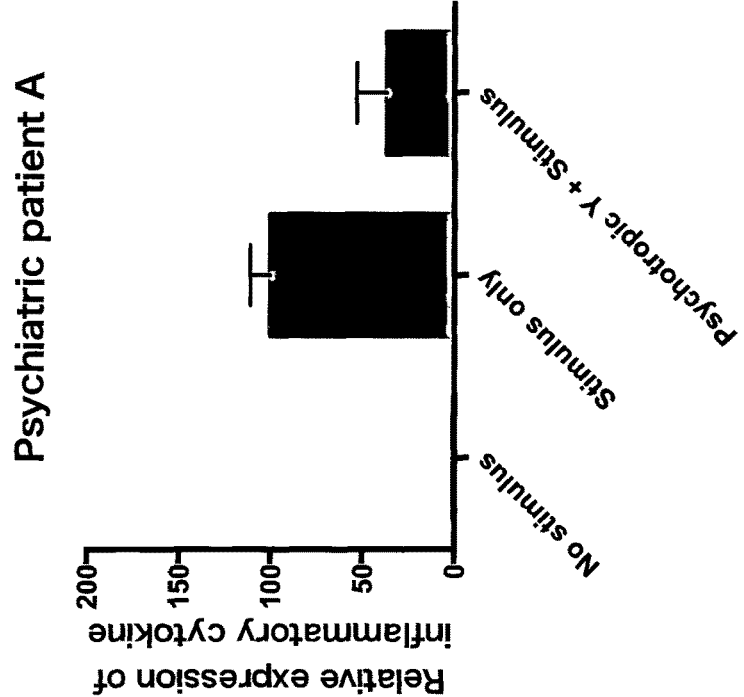

FIG. 5. Psychotropic response of the iMG cells from psychiatric disorders.

The mRNA expression of inflammatory cytokine was compared in different psychiatric disorders. The iMG cells were incubated with psychotropic Y and/or stimulator (IFN-γ), and extracted RNA was analyzed by qRT-PCR (n=2-4). Fold changes are depicted in mRNA levels after stimulation compared with non-stimulated control. Psychotropic response was different between two kinds of psychiatric disorders. Error bars, SEM.

DETAILED DESCRIPTION OF THE INVENTION

Hereinafter, the present invention will be described in detail. The scope of the present invention should not be limited by these descriptions, and may appropriately be modified and carried out apart from the following examples without departing from the spirit of the invention. The present specification incorporates the entire specification of Japanese Patent Application No. 2014-002129 to which the present application claims priority. In addition, all of the prior art documents and laid-open publications, patent publication and other patent documents cited herein are incorporated herein by reference.

The present invention relates to a method of inducing microglial cells, wherein said method comprises the steps of: i) isolating monocytes derived from a subject and ii) culturing said cells in the presence of GM-CSF and IL-34. Further, the present invention relates to a method of producing microglial cells from blood cells, wherein said method comprises the steps of: i) culturing blood cells derived from a subject in the presence of GM-CSF and IL-34, and ii) collecting microglial cells from the culture.

Microglia have long been implicated in various neurological and psychiatric disorders in human postmortem and rodent studies. Especially, Nasu-Hakola disease (NHD) is suggested to be directly caused by microglial dysfunction. However, dynamic actions of microglia in living human brain have not been clarified due to a lack of studies dealing with in situ microglia. Herein, we present a novel technique for developing induced microglial (iMG) cells from human blood cells. An optimized cocktail of cytokines converted human purified monocytes into iMG cells within 14 days. The iMG cells have microglial characterizations; expressing microglial markers, forming ramified morphology, and phagocytic activity which is accompanied with cytokine releases. We developed iMG cells from a patient of NHD and observed that these cells express delayed but strong inflammatory responses compared with those from healthy volunteers. Altogether, the iMG-technique will promise to uncover unresolved aspects of human microglia in various brain disorders.

Herein, we show a novel technique of developing induced microglial (iMG) cells easily and quickly from adult human peripheral blood cells. In addition, by utilizing this iMG-technique, we present the first translational analysis of dynamic actions of microglia from a patient of NHD.

Figure 1:
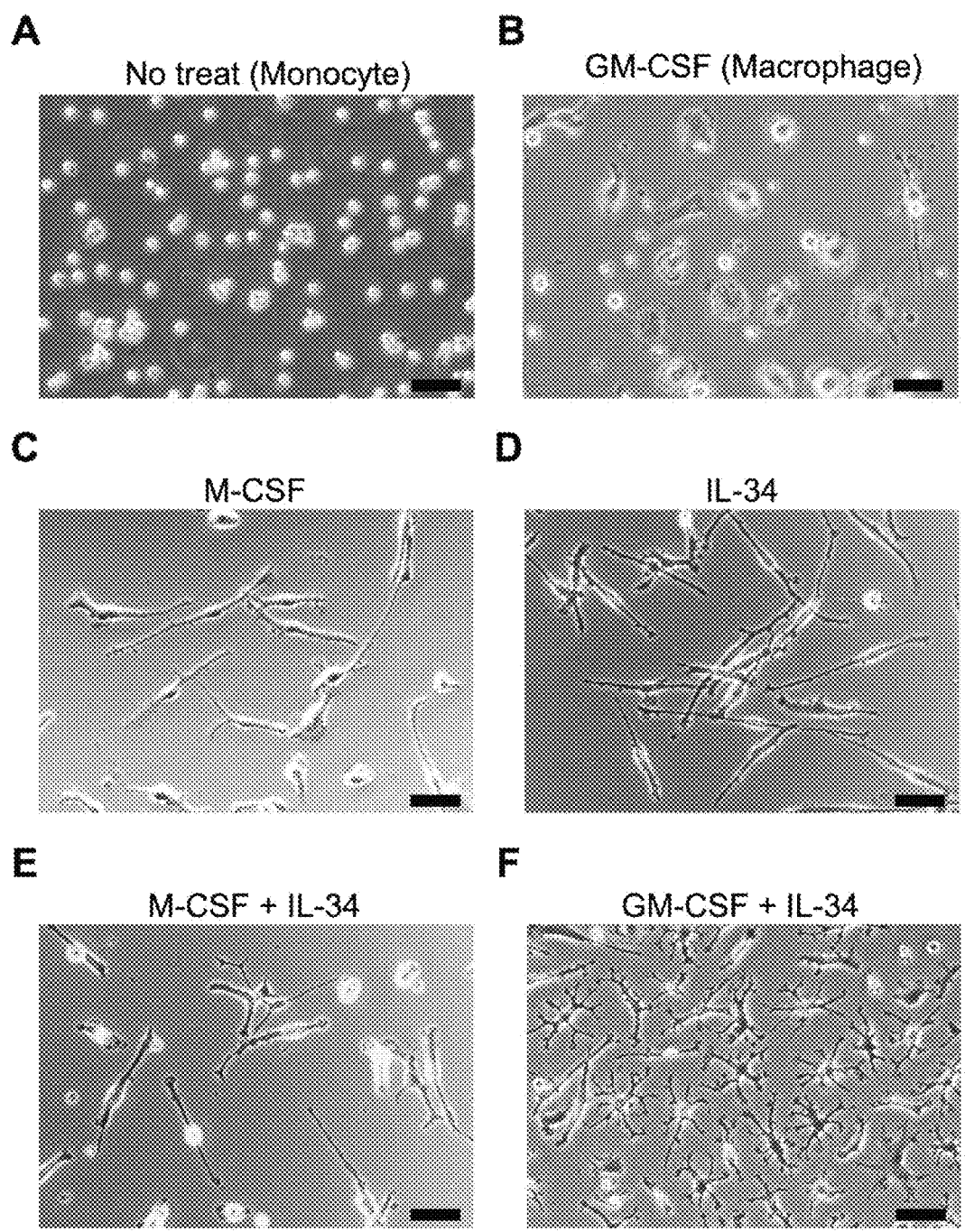
FIG. 1. Inducing ramified microglia from human peripheral monocytes.

To determine what cytokines induce ramified microglia from human peripheral monocytes, we selected and tested the effects of the following candidate cytokines; granulocyte-macrophage colony-stimulating factor (GM-CSF), macrophage colony-stimulating factor (M-CSF) and interleukin (IL)-34, all of which are suggested to be, essential for developing and maintaining ramified microglia (22-25). Untreated monocytes showed round shape (FIG. 1A). Macrophages, induced by GM-CSF (10 ng/ml), were shifted to ameboid morphology on DAY 14 (FIG. 1B). On the other hand, treatment of M-CSF (10 ng/ml) alone or IL-34 (100 ng/ml) alone showed spindle morphology (FIGS. 1C and D), and the cocktail of both cytokines induced more complicated morphology than the single treatment (FIG. 1E). Surprisingly, the cocktail of both GM-CSF (10 ng/ml) and IL-34 (100 ng/ml) induced small soma body bearing numerous branched collaterals (FIG. 1F), which expressed the specific morphology of ramified microglia; small soma with extensive radial ramifications.

Next, we tested whether the ramified microglia-like cells, named induced microglial (iMG) cells, have microglial characterization. In generally, it is difficult to distinguish between macrophage and microglia, because useful and specific microglial markers are very limited. Traditionally, CD11b and CD45 are used as a distinction marker between macrophage and microglia (26). Recently, the phenotype of human microglial cells, isolated from fresh postmortem brain, has been revealed as lower expression of CD14 and CD200R compared to macrophage (27). Thus, we compared the expression level of surface markers between iMG cells and induced macrophage using flow cytometry. The expression level of CD11b on iMG cells did not differ from that on macrophage, while that of CD45 decreased on iMG cells (FIG. 2A). The expression levels of CD14 and CD200R were also more decreased on iMG cells compared to those on macrophage (FIG. 2B), which support that iMG cells have the specific phenotype of microglia (27). On the other hand, Mizutani et al. (28) recently reported the clear-cut distinction between monocyte ($CCR2^{high}$, $CX3CR1^{low}$) and resident microglia ($CCR2^{low}$, $CX3CR1^{high}$) using $CX3CR1^{+/GFP}CCR2^{+/RFP}$ knockin fluorescent protein reporter mice. Therefore, we compared the expression pattern of CCR2 and CX3CR1 between monocyte and iMG cells. Monocytes were stained with bright red fluorescence (CCR2) bearing round or elliptic morphology (FIG. 2C). On the other hand, iMG cells were stained with bright green fluorescence (CX3CR1) bearing highly branched form (FIGS. 2, C and D). The expression ratio (CX3CR1/CCR2) of iMG cells is significantly higher than that of monocyte by immunocytochemistry (FIG. 2E). These results indicate that the cocktail of GM-CSF and IL-34 induce resident microglia (28) from human monocytes.

Melief et al. (27) have also revealed that IL-4 alters the specific gene expression of fresh human microglial cells (HLA-DR, CCR7, CCL18, and CD200R are upregulated, and CD45 and TNF-α are downregulated). Therefore, we assessed the gene expression patterns of iMG cells incubated with IL-4 using the quantitative reverse transcriptase-polymerase chain reaction (qRT-PCR). The expression patterns of the iMG cells are in agreement with the above data using human microglia (27) (FIG. 2F).

Microglia reside as a ramified form, and various molecules activate microglia into an ameboid form, phagocytizing and releasing various cytokines (3), and over activation of microglia induces neuronal damage and various brain pathologies via proinflammatory cytokines such as tumor necrosis factor (TNF)-α (6, 7). To examine whether the iMG cells have these dynamic functions, we tested the phagocytosis ability and the following TNF-α secretion. Interestingly, the iMG cells showed the ability of phagocytosis with morphological changes into an ameboid form (FIG. 3A). Then, we tested the ability of TNF-α production during phagocytosis on the iMG cells, and revealed that the mRNA expression and protein level of TNF-α on the iMG cells during phagocytosis are significantly higher compared to those on non-treated cells (FIGS. 3, B and C).

The above results demonstrated that the iMG cells have dynamic functions of human microglia, and we suppose that the iMG cells have the possibility to be utilized for analyzing the underlying microglial pathophysiology of brain disorders. As the initial step, we conducted the first translational analysis of the iMG cells derived from a patient of NHD. NHD is believed to be caused by microglial dysfunction, while no investigation exists using living human microglial cells from patients of NHD. We analyzed dynamic functions of microglia using the iMG cells from a patient of NHD (141delG in DAP12 gene), after obtaining informed consent (under the permission of the Institutional Review Board of Kyushu University). In agreement with genetic diagnosis, the iMG cells from NHD showed significantly lower expression of DAP12 than those from healthy control, and there was no difference in TREM2 expression (FIG. 4A). Interestingly, the production of pro-inflammatory cytokines (TNF-α and IL-6) was delayed in the iMG cells from NHD as compared to those from healthy control after 24 hours. Furthermore, the iMG cells from NHD showed a significantly lower level of anti-inflammatory cytokine (IL-10) than those from healthy control. The production levels of pro-inflammatory cytokines (TNF-α, IL-6, IL-1β and IL-8) had no significant differences between NHD and healthy control after 72 hours (FIG. 4B).

These results indicate that the iMG cells from NHD show slower (24 h) but not weaker (72 h) proinflammatory cytokines' responses compared to those from healthy control, possibly due to the deletion of DAP12. In addition, suppression of IL-10 production from the iMG cells from NHD indicates that human microglia of NHD tend to be shifted to pro-inflammatory reactions compared to those of healthy subjects. DAP12 and TREM2 are responsible genes of NHD, which mediate various important roles such as phagocytosis and cytokine production in osteoclasts, macrophages, dendritic cells and microglia (29). A rodent study showed that deletion of DAP12 induces synaptic impairments due to microglial dysfunction (15). Hamerman et al. (30) demonstrated that macrophage from DAP12-deficient mice increase inflammatory cytokines' responses, which suggest that DAP12-deleted microglia may increase the inflammatory response. These previous reports and our present findings based on the iMG cells from NHD suggest that human microglia of NHD has a potential to induce stronger and long-acting proinflammatory reactions compared to those of healthy human subjects.

In sum, we have shown a novel technique of developing directly induced microglial cells, named iMG, with a combination of GM-CSF and IL-34 from adult human monocytes, easily and quickly without any virus, feeder cells, and genetic engineering. The iMG cells proved to have characterizations of microglial cells, such as expressing $CD11b^{high}/CD45^{low}$ and $CX3CR1^{high}/CCR2^{low}$. Moreover, the iMG cells expressed dynamic functions such as phagocytosis and releasing pro- and anti-inflammatory cytokines. Finally, we revealed the translational utilities of the iMG cells for analyzing the underlying microglial pathophysiology of NHD. We believe that this novel technique will shed new light on solving unknown dynamic aspects of human microglial cells in various brain disorders.

Method of Culturing Blood Cells

The monocyte may be of any species. It is preferably from a rodent origin, or from a human origin. One standard method for isolating monocytes consists in collecting a population of cells from a subject. For example, fluorescence activated cell sorting (FACS) or magnetic beads cell sorting (MACS) may be used to separate the desired monocytes from a cell population from peripheral blood, or PBMCs, cord blood, as well as pleural, peritoneal, or synovial fluids or from various tissues, such as spleen and lymph node. Other methods can include the isolation of monocytes by depletion of non-monocytes cells (negative selection). Kits for isolation of monocytes are commercially available from Miltenyi Biotec, Stem Cells Technologies, Veritas or BD biosciences.

As an alternative method, monocyte progenitor populations may be derived from bone marrow or cord blood and differentiated to monocytes ex vivo by culture in M-CSF.

The method of the present invention comprises a step of expanding the cells in the presence of IL-34 and GM-CSF. Such cytokines are commercially available from SIGMA, STEM CELL TECHNOLOGIES, R&D systems or Pepro-tech. Each cytokine may be added to a culture medium separately, simultaneously or in the form of mixture/cocktail of such cytokines.

The concentration of GM-CSF in the culture medium can amount from 1 ng/ml to 200 ng/ml, preferably 1 ng/ml to 50 ng/ml and in a particularly 5 ng/ml to 20 ng/ml. The concentration of IL-34 in the culture medium can amount from 1 ng/ml to 200 ng/ml, preferably 50 ng/ml to 150 ng/ml and in a particularly 80 ng/ml to 120 ng/ml.

The method of culturing the blood cells in the culture medium may be performed according to standard methods for culturing animal cells. A natural culture medium or a synthetic culture medium can be used as the culture medium. The culture medium for culturing blood cells may be a standard RPMI-1640 culture medium, a DMEM culture medium or a culture medium comprising one of these mediums with the addition of fetal bovine serum. Culturing is normally performed at 37° C. for 1 to 30 days, preferably 1 to 14 days at 5% $CO_2$. During culturing, the culture may be supplemented by antibiotics such as ampicillin or penicillin as required.

Microglial cells may be collected from the culture by standard methods such as flow cytometry or magnetic cell sorting. The microglial cells thus obtained may be used for a kit for screening or evaluating a therapeutic drug for a psychiatric disease or a neurodegenerative disease.

The present invention provides a kit for inducing microglial cells from blood cells comprising IL-34 and GM-CSF. Also, the present invention provides a kit for screening or evaluating a therapeutic drug for a psychiatric disease or a neurodegenerative disease, which comprises a microglial cell obtained above.

In the present invention, culture medium, buffer solution, calf serum, antibiotics, and the like may be included in a kit. An instruction manual showing inducing procedures may also be included.

Method of Screening Therapeutic Drug or the Like for Psychiatric Disease or Neurodegenerative Disease The present invention can provide a method of screening a therapeutic drug for a psychiatric disease or a neurodegenerative disease by using the microglial cell (iMG cell) described above. The present invention can also provide a method of evaluating a responsiveness of a therapeutic drug for a psychiatric disease or a neurodegenerative disease by using the iMG cell described above.

Specifically, the screening method comprises the steps of: causing the iMG cell according to the present invention to make contact with a candidate substance to measure a cellular activity of the cell; and screening a therapeutic drug for a psychiatric or a neurodegenerative disease by using the obtained measurement result as an indicator. According to this screening method, examples of the psychiatric or neurodegenerative diseases include, but not limited to, schizophrenia, mood disorder (e.g. depression, bipolar disorder), dementia (e.g. Alzheimer's disease), autism, amyotrophic lateral sclerosis (ALS), Parkinson's disease, Huntington's chorea, prion disease, multiple sclerosis, and various physical diseases such as autoimmune disorders, atopic disorders and diabetes. In particular, preferable examples include schizophrenia.

Here, the cellular activities of the iMG cell of the present invention are not limited and examples include various activities involved in the functions, properties or the like of the iMG cell. A known method may be employed for measuring such various activities. In the above-described screening method, a preferable cellular activity to be measured is, for example, phagocytosis, proliferation capacity, viability, neurite elongation capability, cytokine production, morphological changes and differentiation capacity.

For example, if the iMG cell of the present invention is caused to make contact with a candidate substance and thereby is assessed to exhibit increased phagocytosis than that of a cell that has not been placed in contact with the candidate substance, the candidate substance may be selected to be a therapeutic drug for a psychiatric disease or a neurodegenerative disease.

If the iMG cell of the present invention is caused to make contact with a candidate substance and thereby is assessed to exhibit higher proliferation rate (proliferation speed) than that of a cell that has not been placed in contact with the candidate substance, the candidate substance may be selected to be a therapeutic drug for a psychiatric disease or a neurodegenerative disease. Similarly, if the iMG cell of the present invention is caused to make contact with a candidate substance and thereby is assessed to exhibit a longer lifetime or higher viability than those of a cell that has not been placed in contact with the candidate substance, the candidate substance may be selected to be a therapeutic drug for a psychiatric disease or a neurodegenerative disease.

If the iMG cell of the present invention is caused to make contact with a candidate substance and thereby is assessed to exhibit higher elongation rate (elongation speed) than that of a cell that has not been placed in contact with the candidate substance, the candidate substance may be selected to be a therapeutic drug for a psychiatric disease or a neurodegenerative disease.

If the iMG cell of the present invention is caused to make contact with a candidate substance and thereby is assessed to exhibit lower production level of inflammatory cytokines (e.g. TNF-α) than that of a cell that has not been placed in contact with the candidate substance, the candidate substance may be selected to be a therapeutic drug for a psychiatric disease and/or a neurodegenerative disease.

If the iMG cell of the present invention is caused to make contact with a candidate substance and thereby is assessed to exhibit higher morphological change than that of a cell that has not been placed in contact with the candidate substance, the candidate substance may be selected to be a therapeutic drug for a psychiatric disease or a neurodegenerative disease. Similarly, if the iMG cell of the present invention is caused to make contact with a candidate substance and thereby is assessed to exhibit higher differentiation activity than that of a cell that has not been placed in contact with the candidate substance, the candidate substance may be selected to be a therapeutic drug for a psychiatric disease or a neurodegenerative disease.

The present invention can provide a method of evaluating a responsiveness of a therapeutic drug for a psychiatric disease or a neurodegenerative disease by using the iMG cell described above.

Specifically, the evaluating method comprises the steps of: causing the iMG cell according to the present invention to make contact with a candidate substance to measure a cellular activity of the cell; and evaluating a responsiveness of a therapeutic drug for a psychiatric or a neurodegenerative disease by using the obtained measurement result as an indicator.

According to this evaluating method, examples of the psychiatric or neurodegenerative diseases include, but not limited to, schizophrenia, mood disorder (e.g. depression, bipolar disorder), dementia (e.g. Alzheimer's disease), autism, amyotrophic lateral sclerosis (ALS), Parkinson's disease, Huntington's chorea, prion disease, multiple sclerosis, and various physical diseases such as autoimmune disorders, atopic disorders and diabetes.

Here, the cellular activities of the iMG cell of the present invention are not limited and examples include various activities involved in the functions, properties or the like of the iMG cell. A known method may be employed for measuring such various activities. In the above-described screening method, a preferable cellular activity to be measured is, for example, phagocytosis, proliferation capacity, viability, neurite elongation capability, cytokine production, morphological changes and differentiation capacity.

For example, if the iMG cell of the present invention is caused to make contact with a candidate substance and thereby is assessed to exhibit increased phagocytosis than that of a cell that has not been placed in contact with the candidate substance, the candidate substance may be evaluated to be an enhancer of microglial activity for a therapeutic drug for a psychiatric disease or a neurodegenerative disease. The candidate substance can be selected as a drug for eliminating amyloid beta (Aβ) present in the brain.

If the iMG cell of the present invention is caused to make contact with a candidate substance and is assessed to exhibit higher proliferation rate (proliferation speed) than that of a cell that has not been placed in contact with the candidate substance, the candidate substance may be selected as a therapeutic drug for a psychiatric disease or a neurodegenerative disease having a basis in decreased microglia. Similarly, if the iMG cell of the present invention is caused to make contact with a candidate substance and is assessed to exhibit longer lifetime or higher viability than those of a cell that has not been placed in contact with the candidate substance, the candidate substance may be selected as a therapeutic drug for a psychiatric disease or a neurodegenerative disease having a basis in decreased microglia.

If the iMG cell of the present invention is caused to make contact with a candidate substance and is assessed to exhibit lower production level of inflammatory cytokine than that of a cell that has not been placed in contact with the candidate substance, the candidate substance may be selected as a therapeutic drug for a psychiatric disease or a neurodegenerative disease.

Another properties such as neurite elongation, morphological changes and differentiation capacity may be evaluated in the same manner as described above.

Cell Therapy

According to the present invention, the iMG cells can be easily and effectively generated in vitro. The ability to obtain a large number of in vitro expanded iMG cells opens new opportunities for the therapeutic field. The invention thus provides a pharmaceutical composition comprising an iMG cell as defined above, in combination with a pharmaceutically acceptable carrier. The invention further provides a pharmaceutical composition which comprises the iMG cell as defined above. It is therefore described a method for treating a subject affected with a psychiatric disease or neurodegenerative disease, which method comprises administering said subject with iMG cells.

Pharmaceutical Compositions

The present invention provides pharmaceutical compositions for the treatment of a psychiatric disease neurodegenerative disease. The psychiatric disease or neurodegenerative disease is at least one selected from the group consisting of schizophrenia, mood disorder, dementia, autism, amyotrophic lateral sclerosis (ALS), Parkinson's disease, Huntington's chorea, prion disease, multiple sclerosis, and physical diseases.

Such compositions comprise a therapeutically effective amount of the iMG according to the present invention, and a pharmaceutically acceptable carrier or excipient. By a "therapeutically effective amount" of a cell as described above is meant a sufficient amount of said cell to treat a disease or disorder at a reasonable benefit/risk ratio applicable to any medical treatment. It will be understood, however, that the total daily usage of compositions of the present invention will be decided by the attending physician within the scope of sound medical judgment. The specific therapeutically effective dose level for any particular patient will depend upon a variety of factors including the disorder being treated and the severity of the disorder; the specific composition employed, the age, body weight, general health and sex; the time of administration and route of administration; the duration of the treatment; drugs used in combination or coincidental with the specific cells employed; and factors well known in the medical arts. Pharmaceutically acceptable carrier or excipient includes but is not limited to saline, buffered saline, dextrose, water, glycerol and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion. In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

EXAMPLES

Example 1

Materials and Methods

Subjects

The present study was conducted in accordance with the World Medical Association's Declaration of Helsinki and was approved by the Ethics Committee of the Graduate School of Medical Sciences, Kyushu University and Osaka University. We recruited a middle-aged female patient, who was diagnosed with Nasu-Hakola disease (141delG in DAP12 gene) in her thirties. Based on informed consents both from the patient and a family member, we took a blood sample. Healthy adult volunteers including an age-matched female were also recruited.

Induction of Induced Microglial (iMG) Cells from Human Peripheral Blood.

Peripheral blood was collected using a heparinized tube from healthy adult volunteers and a patient of NHD. Peripheral blood mononuclear cells (PBMC) were isolated by Histopaque-1077 (Sigma Chemical Co., St. Louis, Mo.) density gradient centrifugation. PBMC were resuspended with RPMI-1640 (Nacalai Tesque, Kyoto, Japan), 10% heat-inactivated fetal bovine serum (FBS; Japan Bio Serum, Hiroshima, Japan) and 1% antibiotics/antimycotic (Invitrogen, Carlsbad, Calif.). PBMC were plated onto culture chambers at density of 4×10⁵ cells/nil and cultured overnight in standard culture conditions (37° C., 5% $CO_2$). After overnight incubation, culture supernatant and non-adherent cells were removed. The adherent cells (monocytes) were cultured with RPMI-1640 Glutamax (Invitrogen) supplemented with 1% antibiotics/antimycotic and a mixture of the following candidate cytokines; recombinant human GM-CSF (10 ng/ml; R&D Systems, Minneapolis, Minn.), recombinant human IL-34 (100 ng/ml; R&D Systems) and M-CSF (10 ng/ml; Peprotec, Rocky Hill, N.J.) in order to develop iMG cells. We also developed induced macrophage from human monocytes; monocytes were cultured with RPMI-1640 Glutamax supplemented with 1% antibiotics/antimycotic and recombinant human GM-CSF (10 ng/ml). All cells were cultured in standard culture conditions for up to 14 days.

Cell Morphology

Morphological changes of cytokine treated cells were examined using phase-contrast microscopy (TS 100-F; Nikon Instech, Tokyo, Japan). Images were taken with DS-Vi1 digital camera (Nikon Instech) and DS-L3 control unit (Nikon Instech).

Flow Cytometry

Flow cytometry was performed using a FACS Aria (BD Biosciences, Bedford, Mass.) with FACS Diva software (BD Biosciences). Flow cytometry data were analyzed using FlowJo software (Tree Star, San Carios, Calif.). Fluorochrome conjugated monoclonal antibodies specific for human CD11b (APC-Vio770; Miltenyi Biotec, Gladbach, Germany), CD14 (FITC; Sigma), CD45 (PE; Miltenyi Biotec) and CD200R (Alexa647; Serotec, Oxford, UK) were used to iMG phenotyping. Induced macrophage and iMG cells were cultured in 6-well plate (Corning, N.Y.) at a density of 4×10⁵ cells/ml. Cells were harvested by non-enzymatic cell dissociation solution (Sigma) and cell lifter (Corning). The cells were washed with MACS buffer (Miltenyi Biotec) and incubated for 5 minutes at 4° C. in FcR-blocking reagent (Miltenyi Biotec). Antibodies were incubated with cell suspension for 30 minutes at 4° C., washed with calcium-magnesium-free phosphate-buffered saline (PBS(−)), resuspended and fixed with 1% paraformaldehyde (Wako, Osaka, Japan) in PBS(−). The fluorescence intensity of the cells was measured.

Immunocytochemistry

In immunocytochemistry, iMG cells and monocytes were cultured in 8-well chambers (LabTec chamber slide system; Nalge Nunc International, Rochester, N.Y.) at a density of 4×10⁵ cells/ml. These cells were fixed with 4% paraformaldehyde (Wako) for 20 minutes and the rinsed thrice with PBS(−) for 5 minutes. Indirect immunofluorescence was performed using the following antibodies: rabbit anti-CX3CR1 antibody (1:500 dilution; Immuno-Biological Laboratories, Gunma, Japan) and mouse anti-CCR2 antibody (1:500 dilution; R&D Systems). Cells were incubated in primary antibodies diluted in 0.1% Triton-X 100 in PBS containing 5% normal goat serum at 4° C. overnight. After rinsing thrice with PBS(−) for 5 min, Alexa488- or Alexa546-conjugated secondary antibodies (Invitrogen) were used for detection. Fluorescent images were taken with a confocal laser scanning microscope (LSM-780; Carl Zeiss, Jena, Germany). The ratio of CX3CR1 to CCR2 was calculated by the fluorescent intensity of each fluorochrome using the Zeiss ZEN software. At least nine fields were analyzed.

Quantitative Real Time-Polymerase Chain Reaction (qRT-PCR)

To assess the gene expression in iMG cells after treated with IL-4 and during phagocytosis, we performed qRT-PCR using a LightCycler 480 system (Roche Diagnostics, Mannheim, Germany). IL-4 (40 ng/ml; Peprotec) or latex beads-rabbit IgG-FITC solution (Cayman Chemical) was added to the iMG cells and incubated for 72 hours in standard culture conditions. After incubation, iMG cells were washed and extracted the total RNA using a High Pure RNA Isolation kit (Roche Diagnostics) according to the manufacturer's protocol, and subjected to cDNA synthesis using a Transcriptor First Strand cDNA Synthesis kit (Roche Diagnostics). qRT-PCR for HLA-DR, CD45, TNF-α, CCR7, CCL18 CD200R and TNF-α was performed using each primers (Table 1). Beta 2-microglobulin of Universal ProbeLibrary (Roche Diagnostics) was used as a house-keeping control gene.

TABLE 1

| Primer | Sequences | SEQ ID NO |
|---|---|---|
| HLA-DR-F | 5′-TTCAGGAATCAGAAAGGACACTC-3′ | 1 |
| HLA-DR-R | 5′-TCTGCATTTCAGCTCAGGAA-3′ | 2 |
| CD45-F | 5′-AGTCAAAGTTATTGTTATGCTGACAGA-3′ | 3 |
| CD45-R | 5′-TGCTTTCCTTCTCCCCAGTA-3′ | 4 |
| TNF-α-F | 5′-CAGCCTCTTCTCCTTCCTGAT-3′ | 5 |
| TNF-α-R | 5′-GCCAGAGGGCTGATTAGAGA-3′ | 6 |
| CCR7-F | 5′-GGGGAAACCAATGAAAAGC-3′ | 7 |
| CCR7-R | 5′-ACCTCATCTTGACACAGGCATA-3′ | 8 |
| CCL18-F | 5′-ATGGCCCTCTGCTCCTGT-3′ | 9 |
| CCL18-R | 5′-AATCTGCCAGGAGGTATAGACG-3′ | 10 |
| CD200R-F | 5′-TGGGATTCATTTGGTTGTTG-3′ | 11 |
| CD200R-R | 5′-CAACTGGAGTAGATTCTGTTTTATTCA-3′ | 12 |
| DAP12-F | 5′-GAGACCGAGTCGCCTTATCA-3′ | 13 |
| DAP12-R | 5′-CTGTGTGTTGAGGTCGCTGT-3′ | 14 |
| TREM2-F | 5′-TCTGAGAGCTTCGAGGATGC-3′ | 15 |
| TREM2-R | 5′-GGGGATTTCTCCTTCCAAGA-3′ | 16 |

In iMG cells of NHD, we examined the expression of DAP12 and TREM2 gene by qRT-PCR. The iMG cells from healthy control and NHD patient were washed and extracted the total RNA, and qRT-PCR was performed using each primers (Table 1). Beta 2-microglobulin was used as a house-keeping control gene.

Phagocytosis

Phagocytosis was examined by fluorescent microscopy using Phagocytosis Assay kit (Cayman Chemical, Ann Arbor, Mich.) according to the manufacturer's protocol. iMG cells were cultured in 8-well chambers (Nalge Nunc International) at a density of 4×10⁵ cells/ml. We added 50 µl of the latex beads-rabbit IgG-FITC solutions to each well of the chamber, and incubated the cells in standard culture conditions for 24 hours. After discarding the supernatant by careful aspiration, we quenched surface-bound fluorescence, added 125 µl of trypan blue solution to each well of the chamber, and incubated for two minutes at room temperature. Each well was analyzed by using a fluorescence microscope (Olympus IX-71, Tokyo, Japan) and DP71 digital camera system (Olympus).

Cytokine Measurement

Secretion of Cytokines (TNF-α, IL-1β, IL-6, IL-8 and IL-10) during phagocytosis was measured from culture supernatants using Cytometric Beads Array System (CBA; BD Biosciences) according to manufacturer's protocol. Latex beads-rabbit IgG-FITC solution (Cayman Chemical) was added to the iMG cells and incubated for 24 or 72 hours in standard culture conditions. After incubation, culture supernatants were centrifuged at 10000×g for 10 minutes and kept frozen at −80° C. until assayed. The culture supernatants were incubated with the cytokine capture beads and PE-conjugated detection antibodies for 3 hours at room temperature. Afterwards, the capture beads were washed and measurement data were acquired using a FACS Canto™ flow cytometer (BD Biosciences). The data analysis was performed using FCAP Array software (BD Biosciences).

Statistical Analysis

Comparisons between groups were done by two-tailed Student's t-test.

Example 2

Induction of iMG Cells

Peripheral blood was collected using a heparinized tube from vein such as brachial vein. Peripheral blood mononuclear cells (PBMCs) were isolated by density gradient centrifugation. Isolated monocytes from PBMCs were incubated with culture medium (RPMV10% FBS/1% Antibiotics). After overnight incubation, culture supernatant was removed. The adherent cells were cultured with induction medium (RPMI-Glutamax/IL-34(100 nM)/GM-CSF (10 nM)/1% Antibiotics). Cells were cultured in standard culture conditions (37° C./5% $CO_2$) for up to 14 days.

Drug Response Assay

After 14 days incubation, culture medium were changed to new induction medium. Cells were cultured in standard culture conditions for few days. Culture medium were changed to basal medium (RPMI-Glutamax/1% Antibiotics). Test drugs were added into culture chamber. Cells were incubated with test drugs. Drug responses were analyzed by each assay. The iMG cells are able to perform many cell-based assay such as gene expression, protein expression, phagocytosis and migration. Culture supernatant is also able to measure the cytokines and metabolites.

Results

FIG. 5 shows the psychotropic response of the iMG cells from psychiatric disorders.

The mRNA expression of inflammatory cytokines which are produced by microglia and impair the surrounding neurons was compared in patients affected by different psychiatric disorders. The iMG cells were obtained from these patients and incubated with a clinically-used psychotropic drug Y and/or stimulator (IFN-γ), and extracted RNA was analyzed by qRT-PCR. Expression of the inflammatory cytokines against an exogenous stimulus was analyzed as a basis for evaluation. Fold changes are depicted in mRNA levels after stimulation in comparison with a non-stimulated control. The psychotropic response was different between two kinds of psychiatric disorders. That is, the psychotropic effect (i.e. a suppressed expression of the inflammatory cytokines) of drug Y was observed in patient A, but not in patient B. These results indicate that the iMG cells are not homogeneous and have unique characteristics depending on each patient. Therefore, the iMG cells of the present invention can be used as a tool for evaluating a sensitivity or responsiveness of drugs against microglia.

REFERENCES

1. F. Ginhoux et al., Science 330, 841 (2010).
2. A. Nimmerjahn, F. Kirchhoff, F. Helmchen, Science 308, 1314 (2005).
3. H. Kettenmann, U. K. Hanisch, M. Noda, A. Verkhratsky, Physiol Rev 91, 461 (2011).
4. R. M. Ransohoff, V. H. Perry, Annu Rev Immunol 27, 119 (2009).
5. M. B. Graeber, Science 330, 783 (2010).
6. M. L. Block, L. Zecca, J. S. Hong, Nat Rev Neurosci 8, 57 (2007).
7. U. K. Hanisch, H. Kettenmann, Nat Neurosci 10, 1387 (2007).
8. T. A. Kato et al., Curr Med Chem 20, 331 (2013).
9. H. P. Hakola, Acta Psychiatr Scand Suppl 232, 1 (1972).
10. T. Nasu, Y. Tsukahara, K. Terayama, Acta Pathol Jpn 23, 539 (1973).
11. M. Kaneko, K. Sano, J. Nakayama, N. Amano, Neuropathology 30, 463 (2010).
12. J. Paloneva et al., Neurology 56, 1552 (2001).
13. J. Paloneva et al., Nature Genet 25, 357 (2000).
14. J. Paloneva et al., Am J Hum Genet 71, 656 (2002).
15. A. Roumier et al., J Neurosci 24, 11421 (2004).
16. J. Satoh et al., Neuropathology 31, 363 (2011).
17. V. B. Mattis, C. N. Svendsen, Lancet Neurol 10, 383 (2011).
18. J. T. Dimos et al., Science 321, 1218 (2008).
19. U. Pfisterer et al., Proc Natl Acad Sci USA 108, 10343 (2011).
20. L. Qiang et al., Cell 146, 359 (2011).
21. Z. P. Pang et al., Nature 476, 220 (2011).
22. Y. Wang et al., Nature immunol 13, 753 (2012).
23. F. Aloisi, R. De Simone, S. Columba-Cabezas, G. Penna, L. Adorini, J Immunol 164, 1705 (2000).
24. B. Erblich, L. Zhu, A. M. Etgen, K. Dobrenis, J. W. Pollard, PloS One 6, e26317 (2011).
25. S. Nandi et al., Dev Biol 367, 100 (2012).
26. J. D. Sedgwick et al., Proc Natl Acad Sci USA 88, 7438 (1991).
27. J. Melief et al., Glia 60, 1506 (2012).
28. M. Mizutani et al., J Immunol 188, 29 (2012).
29. A. Paradowska-Gorycka, M. Jurkowska, Hum Immunol 74, 730 (2013).
30. J. A. Hamerman, N. K. Tchao, C. A. Lowell, L. L. Lanier, Nat Immunol 6, 579 (2005).

The invention claimed is:

1. A method of producing microglial cells, comprising culturing blood cells in the presence of interleukin-34 (IL-34) and granulocyte-macrophage colony stimulating factor (GM-CSF), and collecting microglial cells from the culture.

2. The method of claim 1, wherein the blood cells are human peripheral monocytes.

3. The method of claim 1, wherein a concentration of IL-34 is 1-200 ng/ml.

4. The method of claim 1, wherein a concentration of GM-CSF is 1-200 ng/ml.

5. A method of evaluating a responsiveness to a therapeutic drug and/or of screening a therapeutic drug for a psychiatric disease or a neurodegenerative disease, comprising the steps of:

producing microglial cells by culturing blood cells in the presence of interleukin-34 (IL-34) and granulocyte-macrophage colony stimulating factor (GM-CSF), and collecting microglial cells from the culture; and causing the microglial cells produced to make contact with a candidate substance to measure a cellular activity of the cells produced; and using the obtained measurement result as an indicator.

6. The method according to claim 5, wherein the cellular activity is at least one selected from the group consisting of phagocytosis, proliferation capacity, viability, neurite elongation capability, cytokine production, morphological changes and differentiation capacity.

7. The method according to claim 5 or 6, wherein the psychiatric disease or neurodegenerative disease is at least one selected from the group consisting of schizophrenia, mood disorder, dementia, autism, amyotrophic lateral sclerosis (ALS), Parkinson's disease, Huntington's chorea, prion diseases, multiple sclerosis, and autoimmune disorders.

* * * * *